(12) United States Patent
Anderson et al.

(10) Patent No.: US 9,987,056 B2
(45) Date of Patent: Jun. 5, 2018

(54) SURGICAL INSTRUMENTS

(71) Applicant: DEPUY IRELAND UNLIMITED COMPANY, County Cork (IE)

(72) Inventors: James Anderson, Leeds (GB); Gary Moore, Wetherby (GB); Ivan Green, Leeds (GB)

(73) Assignee: DePuy Ireland Unlimited Company, Ringaskiddy, County Cork (IE)

( * ) Notice: Subject to any disclaimer, the term of this patent is extended or adjusted under 35 U.S.C. 154(b) by 721 days.

(21) Appl. No.: 14/403,691

(22) PCT Filed: May 28, 2013

(86) PCT No.: PCT/GB2013/051398
§ 371 (c)(1),
(2) Date: Nov. 25, 2014

(87) PCT Pub. No.: WO2013/179012
PCT Pub. Date: Dec. 5, 2013

(65) Prior Publication Data
US 2015/0164562 A1    Jun. 18, 2015

(30) Foreign Application Priority Data

Jun. 1, 2012 (GB) .................................. 1209809.1
Mar. 15, 2013 (GB) .................................. 1304726.1

(51) Int. Cl.
*A61B 17/88* (2006.01)
*A61B 17/70* (2006.01)
(Continued)

(52) U.S. Cl.
CPC ...... *A61B 17/7098* (2013.01); *A61B 17/8816* (2013.01); *A61B 17/8827* (2013.01);
(Continued)

(58) Field of Classification Search
CPC ............ A61F 2/4601; A61F 2002/4625; A61F 2002/4602; A61F 2002/4627; A61F 2/243;
(Continued)

(56) References Cited

U.S. PATENT DOCUMENTS 5,454,365 A * 10/1995 Bonutti .............. A61B 17/0218
600/204
5,554,191 A * 9/1996 Lahille ............... A61B 17/1671
411/55
(Continued)

FOREIGN PATENT DOCUMENTS

| WO | WO 2005107627 | 11/2005 |
|---|---|---|
| WO | WO 2010097633 | 9/2010 |
| WO | WO 2010097636 | 9/2010 |

*Primary Examiner* — David Bates

(57) ABSTRACT

A kit of parts for inserting a deformable implant into a cavity in a bone of a patient is described. An inserter instrument (1) comprises a body (100) having a cavity extending along a longitudinal axis from a distal end to a proximal end. An attachment mechanism (108) is provided at the distal end and to which a deformable implant can be releasably attached. A drive mechanism (132) is provided at the proximal end of the body. A push rod (150) is freely and slidably arranged within the cavity and has a distal end engageable with a part of the deformable implant and a proximal end abutable by the drive mechanism. The drive mechanism is operable to drive the push rod toward the distal end of the body. The kit also includes an impactor (210) dimensioned for slidable engagement within the cavity.

13 Claims, 5 Drawing Sheets

(51) Int. Cl.
*A61B 17/00* (2006.01)
*A61B 90/00* (2016.01)

(52) U.S. Cl.
CPC ............... *A61B 2017/00867* (2013.01); *A61B 2090/034* (2016.02); *A61B 2090/062* (2016.02)

(58) Field of Classification Search
CPC . A61F 2/2466; A61B 17/885; A61B 17/8852; A61B 17/92
See application file for complete search history.

(56) References Cited

U.S. PATENT DOCUMENTS

| | | | | |
|---|---|---|---|---|
| 5,976,139 A * | 11/1999 | Bramlet | ............ | A61B 17/1659 606/282 |
| 6,746,451 B2 * | 6/2004 | Middleton | ......... | A61B 17/1617 606/180 |
| 8,287,538 B2 * | 10/2012 | Brenzel | ............ | A61B 17/7225 606/62 |
| 8,562,607 B2 * | 10/2013 | Truckai | ............ | A61B 17/1615 606/79 |
| 8,784,421 B2 * | 7/2014 | Carrison | ............ | A61B 17/1604 606/113 |
| 8,961,518 B2 * | 2/2015 | Taylor | ............... | A61B 17/1617 606/79 |
| 9,101,430 B2 * | 8/2015 | Muller | ............... | A61B 17/8855 |
| 9,730,746 B2 * | 8/2017 | Auyoung | ........... | A61B 17/8855 |
| 2004/0098017 A1 * | 5/2004 | Saab | ................. | A61B 17/8855 606/192 |
| 2006/0116690 A1 * | 6/2006 | Pagano | ................ | A61B 17/025 606/93 |
| 2007/0088436 A1 * | 4/2007 | Parsons | .............. | A61B 17/8858 623/17.11 |
| 2007/0282443 A1 * | 12/2007 | Globerman | ........ | A61B 17/1637 623/17.11 |
| 2009/0005782 A1 * | 1/2009 | Chirico | ............. | A61B 17/1617 606/63 |
| 2009/0012564 A1 * | 1/2009 | Chirico | ............. | A61B 17/1671 606/246 |
| 2009/0149956 A1 * | 6/2009 | Greenhalgh | ....... | A61B 17/7094 623/17.11 |
| 2009/0228093 A1 * | 9/2009 | Taylor | ................... | A61F 2/2418 623/1.12 |
| 2009/0292323 A1 * | 11/2009 | Chirico | ............. | A61B 17/8858 606/86 R |
| 2010/0249785 A1 * | 9/2010 | Betts | ............... | A61B 17/1617 606/79 |
| 2011/0282127 A1 * | 11/2011 | Cui | ...................... | A61F 2/2487 600/16 |
| 2011/0313537 A1 | 12/2011 | Anderson | | |
| 2012/0071977 A1 | 3/2012 | Oglaza | | |
| 2014/0135780 A1 * | 5/2014 | Lee | ...................... | A61F 2/4601 606/94 |

* cited by examiner

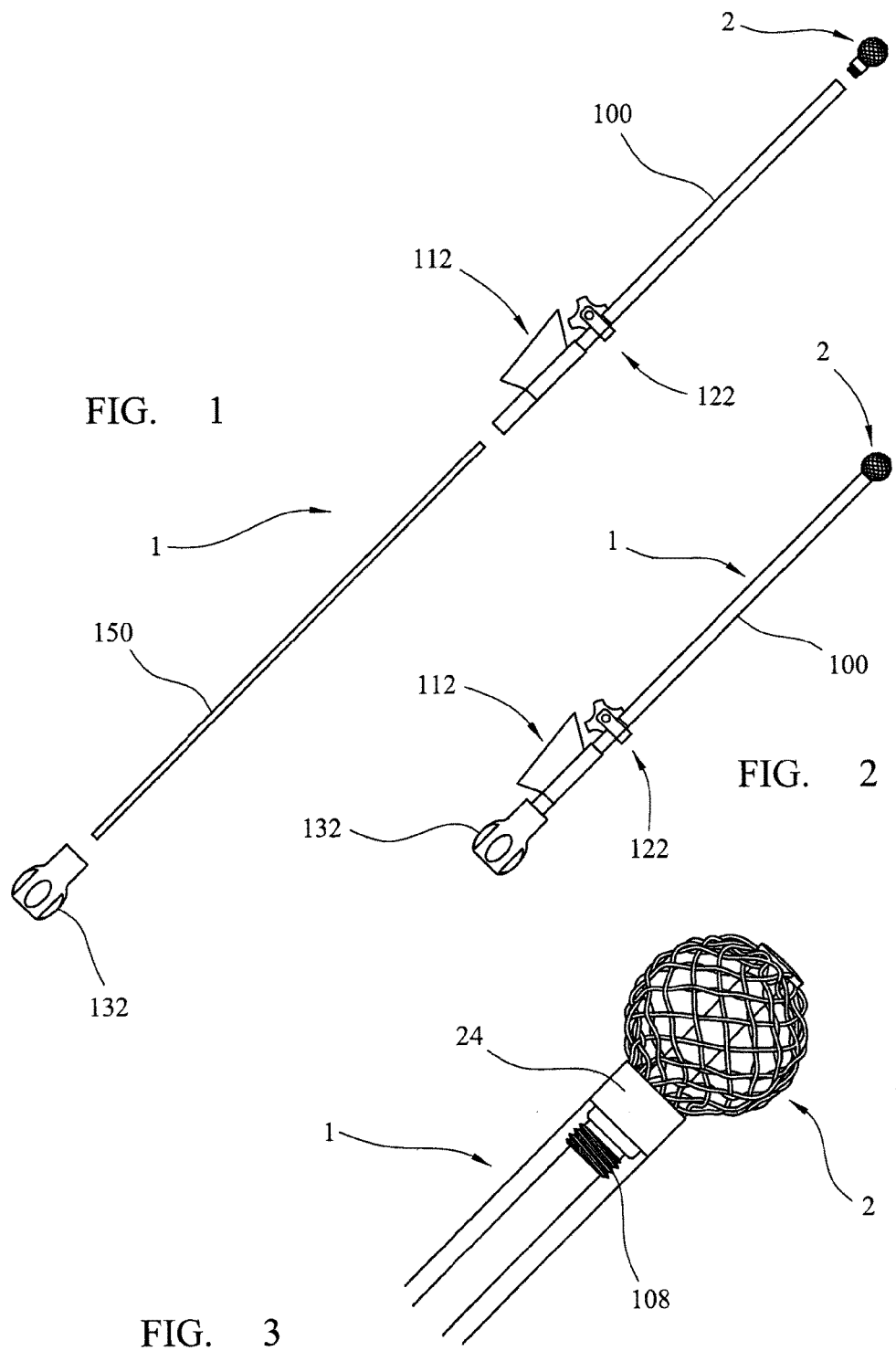

SURGICAL INSTRUMENTS

CROSS REFERENCE TO RELATED APPLICATION

This application is a National Stage 35 U.S.C. 371 of International Patent Application No. PCT/GB2013/051398 filed May 28, 2013 which claims priority to United Kingdom Patent Application Nos. GB1209809.1, filed Jun. 1, 2012 (now abandoned) and GB1304726.1, filed Mar. 15, 2013 (now abandoned).

The present invention relates to a surgical instrument and in particular to a surgical instrument and kit of parts for inserting an implant component into a cavity in a bone of a patient.

WO 2010/097636 describes a support structure implant and assembly, including an instrument, for deploying such an implant. The handling, insertion, deployment and subsequent use of deformable implants can require significant care, for example in order to ensure that the implant is correctly inserted and/or positioned within the bone cavity and/or does not move within the bone cavity after implantation and as it is being used, or otherwise interacted with, during subsequent surgical steps in order to complete the surgical procedure for which the implant is intended.

Therefore instrumentation to increase the reliability and/or ease of insertion and/or deployment of deformable implants would be advantageous.

A first aspect of the invention provides an inserter instrument for inserting a deformable implant into a cavity in a bone of a patient. The inserter instrument can comprise a body having a cavity extending along a longitudinal axis of the body from a distal end to a proximal end. An attachment mechanism can be provided at the distal end, to which a deformable implant can be releasably attached. The inserter instrument can include a drive mechanism at the proximal end of the body. The inserter instrument can further comprise a push rod freely and slidably arranged within the cavity. A distal end can be engageable with a part of the deformable implant. A proximal end can be abutable by the drive mechanism. The drive mechanism is operable to drive the push rod toward the distal end of the body.

The instrument uses a freely sliding push rod actuable by a drive mechanism which can abut against a free end of the push rod and hence has a particularly simple construction which facilitates assembly, use, disassembly, cleaning and ease of manufacture of the instrument.

A part of the drive mechanism can be removable from the instrument. The push rod can be slideably removable from the instrument via the proximal end of the body. Hence, the push rod can be removed from the instrument while the instrument is still attached to the implant. Hence, the body can be used for a secondary purpose, such as the transfer of bone graft to the implant, without interfering with the placement of the implant.

The push rod can have a longitudinal length greater than a longitudinal length of the cavity of the body. Preferably the longitudinal length of the push rod is at least the length of the cavity and the length of rod deformable implant in the direction of the longitudinal axis. Preferably the longitudinal length of the push rod is at least the length of the cavity and the length of rod deformable implant in its maximally deformed state in the direction of the longitudinal axis. More preferably the longitudinal length of the push rod is greater than the length of the cavity and the length of rod deformable implant in its maximally deformed state in the direction of the longitudinal axis.

The length of the push rod can be greater than the length of the cavity and the length of the implant in the direction of the longitudinal axis (in either the deployed or the deformed state) such that a portion of the push rod is proud of the proximal end of the body and hence easily abutable by a part of the drive mechanism.

The drive mechanism can include a pair of matching threads and a surface abutable against the proximal end of the push rod and caused to translate along the longitudinal axis by the threads. The drive mechanism can include an internal thread and an external thread co-operating with the internal thread. The drive mechanism can include a cap. A part of the cap, such as an inner surface, can be arranged to abut the proximal end of the push rod. The cap can includes a one of the internal thread and the external thread. The proximal end of the body can include the other of the internal thread and the external.

The external thread can be provided on an outer surface of the body at the proximal end of the body. The internal thread can be provided on an inner surface of the cap.

The cap can include a grip formation disposed on an outer surface around its periphery providing a grip for rotation of the cap about the longitudinal axis by a user.

The cap can be in the form of a rotatable knob.

The inserter instrument can further comprise a stop arranged to limit the extent of travel of the push rod within the body toward the distal end. The stop can comprise a member extending from the push rod. The stop can further comprise a channel in an inner wall of the body and having an end wall. The member can be arranged to slide within the channel and to abut against the end wall. The member and channel can further co-operate to prevent rotation of the push rod about the longitudinal axis. The stop can further be arranged to prevent binding of the drive mechanism.

The inserter instrument can further comprise a hopper. The hopper can be attached to an upper surface of the body. The hopper can include a lower opening in communication with the cavity.

The inserter instrument can further comprise a discontinuity in its outer surface. The discontinuity can provide a vent in use to prevent or reduce any increase or decrease in pressure within the bone. The discontinuity can be in the form of a flat surface and the flat surface can be on an upper part of the instrument. The discontinuity can extend along the instrument body and can extend for at least a quarter, a half, two thirds or three quarters of the length of the body. The discontinuity can extend to the distal end of the body. The discontinuity can extend from the distal end of the body to a scale on the body or to a stop on the body or to a stop attachment location on the body.

The inserter instrument can include a scale. The scale can include a plurality of indicia on an outer surface of the body corresponding to or indicating different depths of insertion of the instrument.

The inserter instrument can further include an adjustable insertion stop attachable to the body, and preferably the scale part, at different longitudinal positions. The insertion stop can act to control the depth of insertion of the inserter instrument.

A second aspect of the invention provides a kit of parts. The kit of parts can comprise an inserter instrument according to the first aspect of the invention and can include any preferred features thereof. The kit of parts can further comprise an impactor dimensioned for slidable engagement within the cavity. The impactor can have a longitudinal length greater than the length of the cavity.

The impactor can include a distal part in the form of a rod. The distal part can have a free end. The impactor can include a proximal part. The proximal part can be in the form of a rod. The impactor can include an intermediate part. The intermediate part can have a form visually distinguishable from the distal and/or proximal parts. The intermediate part can have a form different to the form of the distal and/or proximal parts. The intermediate part can be in the form of a flat beam. The intermediate part can be closer to the distal end than the proximal end. The proximal part can be longer than the distal part or the distal part and the intermediate part. The impactor can include a handle attached to a proximal end of the proximal part. The intermediate part can be arranged between the distal part and the proximal part.

The kit of parts can further comprise a deformable implant including a releasable attachment mechanism. The releasable attachment mechanism can be arranged to cooperate with the attachment mechanism of the distal end of the inserter instrument.

A further aspect of the invention provides an assembly comprising the inserter instrument aspect of the invention, including any preferred features thereof, and a deformable implant.

A further aspect of the invention can include a method of use of the inserter instrument to implant a deformable implant in a bone cavity of a patient.

An embodiment of the invention will now be described in detail, by way of example only, and with reference to the accompanying drawings, in which:

FIG. 1 shows a kit of parts according to the invention and including an inserter instrument according to the invention in a disassembled state;

FIG. 2 shows the inserter instrument and kit of parts shown in FIG. 1 in an assembled state;

FIG. 3 shows a magnified view of a distal end of the assembly shown in FIG. 2;

Like items in different Figures share common reference signs unless indicated otherwise.

With reference to FIG. 1 there is shown an exploded view of an inserter instrument 1 and an implant 2.

FIG. 2 shows the instrument 1 in an assembled state with the implant 2 attached thereto forming an assembly according to an aspect of the invention.

FIG. 3 shows a magnified, partial cross section view of a distal end of the assembly including a distal end of the instrument 1 and the implant 2 attached thereto.

The inserter instrument 1 can be used to deform the implant 2 prior to insertion into a previously prepared bone cavity. When inserted in the bone cavity, the instrument can further be used to allow the deformable implant 2 to retain to its deployed state, as illustrated in FIGS. 1 to 3, in order to provide structural support to the bone cavity.

Figure 4:
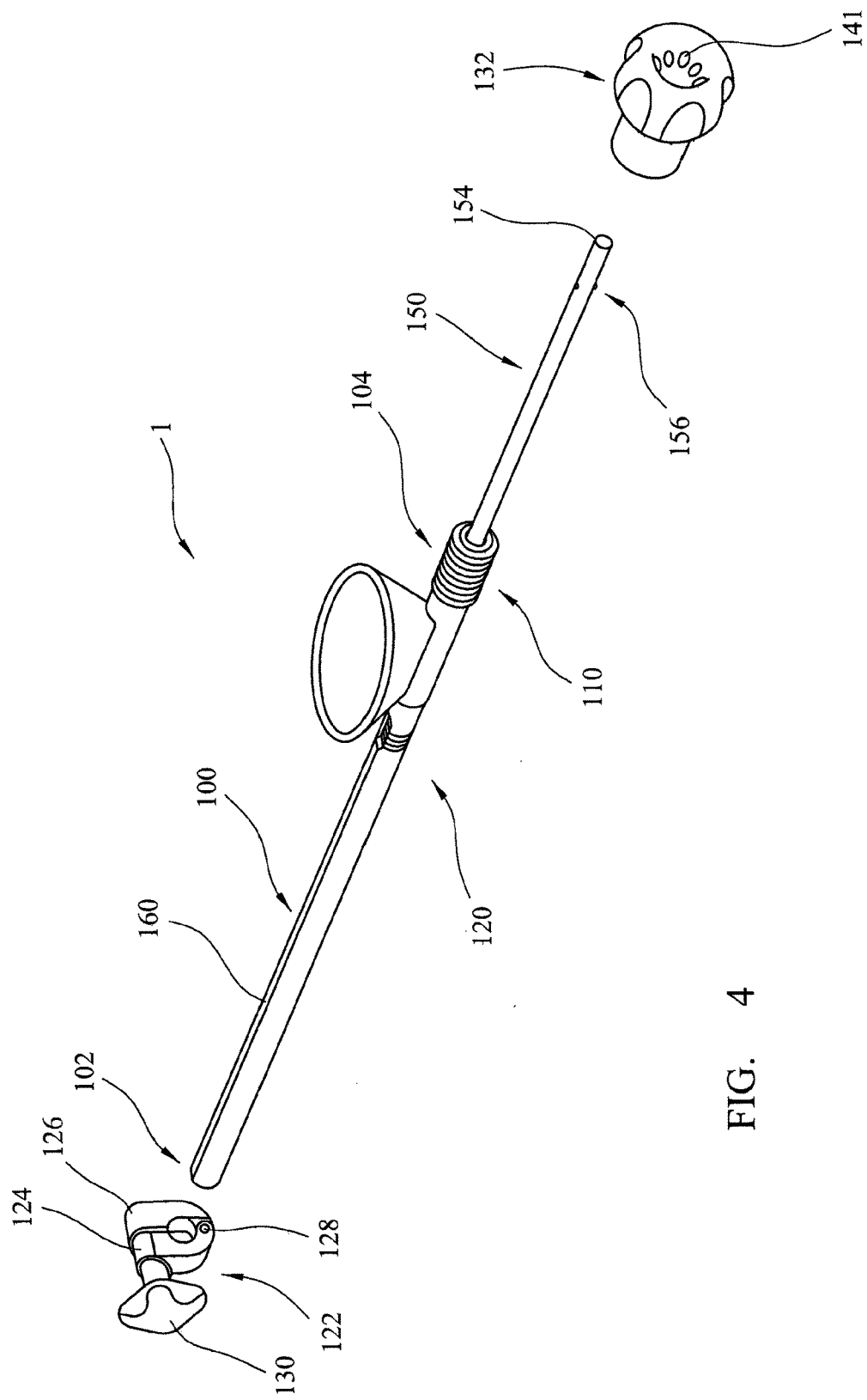
FIG. 4 shows a perspective exploded view of the inserter instrument according to the invention.
Figures 5, 6, 7:
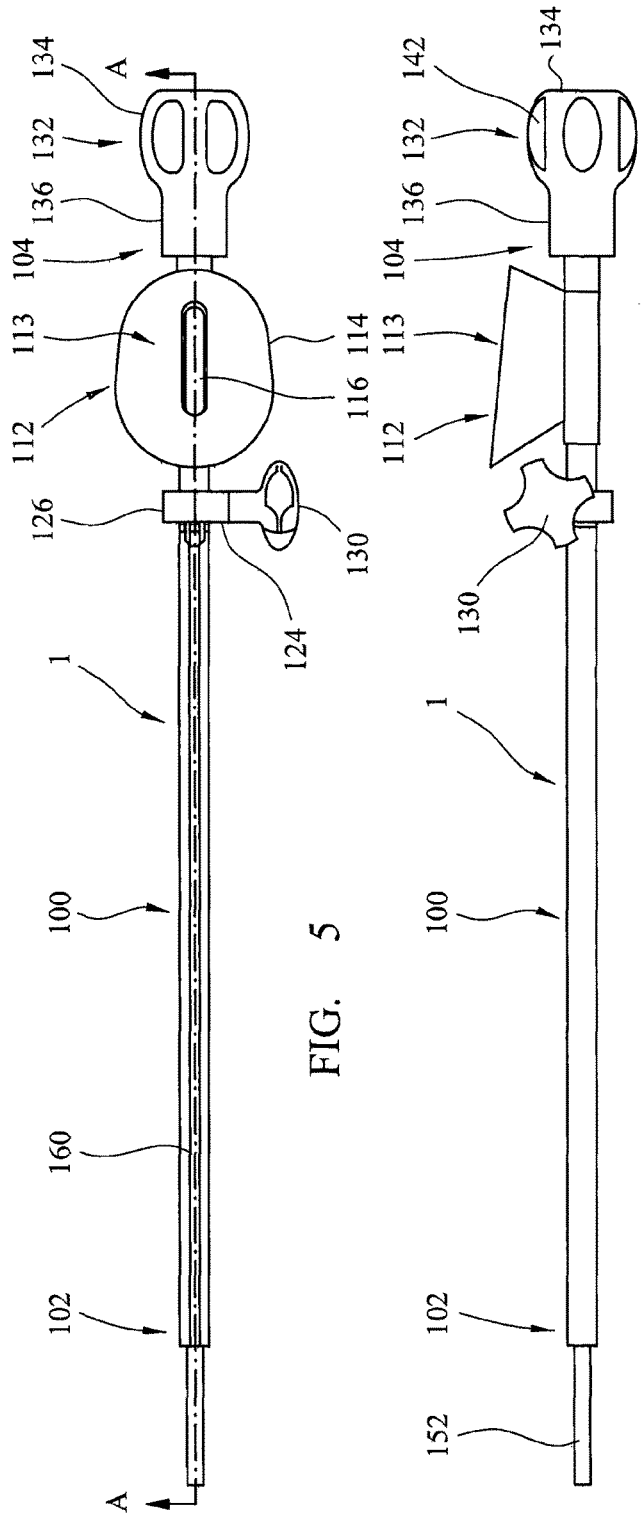
FIG. 5 shows a plan view of the inserter instrument in an assembled state.
FIG. 6 shows a side view of the inserter instrument in an assembled state.
FIG. 7 shows a transverse cross sectional view along the line A-A' of FIG. 5.

FIG. 4 shows an exploded perspective view of the instrument 1 and FIGS. 5, 6 and 7 show respective plan, side and transverse cross sectional views of the instrument 1 in an assembled state.

Instrument 1 includes a body 100 having a generally circular cylindrical form and including a distal 102 and proximal 104 end. A central, longitudinal cavity 106 extends between the proximal and distal ends of the body 100 such that the body has a generally tubular construction. The inner wall of the body 100 which defines longitudinal cavity 106 has a smooth or precision surface finish, for example a honed or gun drilled surface, in order to avoid potential blockage of the cavity 106 by bone graft material during use. The distal end 102 of the tubular body includes an internal thread 108 which forms parts of a releasable attachment mechanism for the implant 2. The proximal end 104 of the body includes an external threaded portion 110 which forms a part of a guide mechanism described in greater detail below.

A hopper 112, for receiving bone graft material, is provided toward the distal end of the body 100. The hopper includes sloped side walls 114 defining an upper opening 113 and which taper toward a lower opening 116 in communication with the longitudinal cavity of the main body 100. Hopper 112 extends in a direction substantially perpendicular to the longitudinal axis of the main body 100. As best illustrated in FIG. 7, an undercut 115 is located at the junction of a forward end of the opening 116 and a lower part of a front wall 117 of the hopper 112. The undercut 115 helps to avoid a user's fingers or gloved fingers from being trapped when feeding bone graft material through the opening into the instrument.

A portion of the body distal to the hopper 112 includes a plurality of markings or indicia, providing a scale. The scale 120 includes a substantially planar surface portion bearing numbers and a corresponding plurality of markings extending circumferentially around the body indicating different potential depths of insertion of the instrument 1.

The instrument 1 also includes an instrument depth stop 122 generally in the form of a clamp and having a pair of jaws 124, 126 connected by a pivot 128 and a threaded knob 130 by which the stop 122 can be clamped about the scale portion 120 of the body at different longitudinal positions.

As mentioned above, a drive mechanism 132 is provided at a proximal end 104 of the instrument 1. The drive mechanism 132 includes a cap 134 including a barrel portion 136 bearing an internal thread 138 dimensioned to cooperate with external thread 110. Cap 134 includes a cavity therein within barrel section 136 and having an interior portion 140 of greater diameter and presenting an end face or wall 140. Cap 134 also includes a plurality of apertures, e.g. aperture 141, passing through the end wall which provide drain holes to facilitate cleaning of the end cap 134 after use. Cap 134 includes a plurality of recessed portions 142 disposed around the periphery of cap 134 and providing a grip formation for a user.

Instrument 1 also includes a push rod 150. Push rod 150 has a distal 152 and proximal 154 end. As best illustrated in FIG. 7, push rod 150 is slidably received within the longitudinal cavity and extends there along, and has a length greater than the length between the proximal and distal ends of the main body 1. As illustrated in FIG. 7, the proximal end 154 of push rod 150 abuts against the inner face 140 of cap 132 and the distal end 152 extends proud of the distal end 102 of the main body 100. Toward the proximal end of the push rod 150, a pin 156 extends in a generally downward direction from the push rod. Pin 156 is received in a recessed channel 158 formed in the main body 1 toward its proximal end 104. Channel 158 includes a closed end face against which pin 156 can abut to prevent further motion of the push rod in the distal direction.

An upper portion of body 100 includes a substantially flat surface 160 extending from the distal end 102 of the body 100 up to the scale 120. The flat surface 160 is a discontinuity in the shape of the outer surface of the body 100 which otherwise has a circular cross section. The discontinuity formed by the flat surface portion creates a vent in use which helps to prevent a seal being caused. This ensures that air can be released during insertion and removal of the instrument, thereby reducing the risk of pressure building up, or a vacuum being formed, within the bone.

Figure 8:
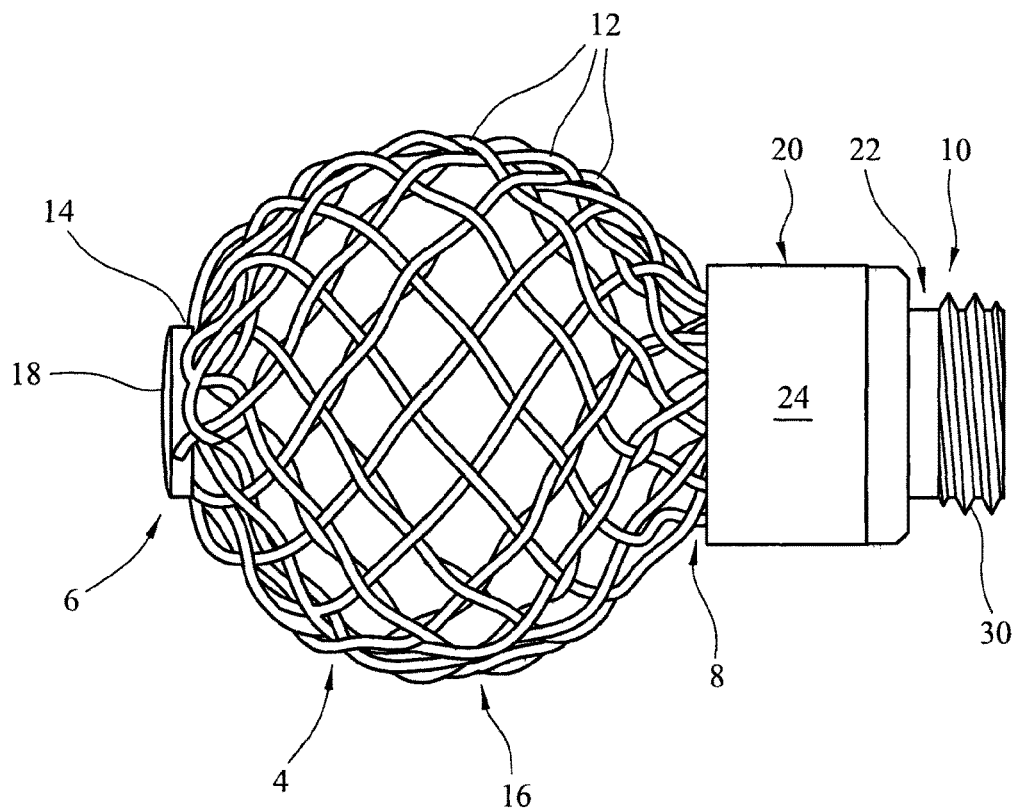
FIG. 8 shows a schematic side view of the deformable implant.

FIG. 8 shows a schematic side view of the deformable implant 2 in greater detail. The construction of a suitable implant is described in greater detail in WO 2010/097636 (International patent application no. PCT/GB2010/050337) which is incorporated herein by reference in its entirety for all purposes.

FIG. 8 shows the stranded support structure implant 2 which can be implanted in a cavity in a bone, to support the bone which defines the cavity. The implant has a spherical portion 4 which is rounded at a first end 6 of the implant, and a cylindrical throat portion 8 at a second end 10 of the implant.

The implant 2 is formed from twelve wires 12 which are formed from a nickel titanium shape memory alloy which has been treated so that it exhibits enhanced elastic properties. The wires have a diameter of 0.5 mm.

Each of the wires is formed into a loop 14. The loops are gathered together at the first end 6 of the implant so that two lengths of each wire extend from the first end. There are therefore 24 lengths of the wires extending from the first end of the implant, which are braided. The configuration of the spherical portion 4 is such that the implant flares outwardly from the first end 6 towards a wide point 16, and tapers inwardly from the wide point towards the throat portion 8.

The implant includes a retainer clip 18 at its first end which engages the twelve loops 14 formed in the wires 12 to control their spacing.

The implant includes a ring clamp 20. The ring clamp 20 comprises an internal support ring 22 and an outer ring 24. The internal support ring 22 is formed from stainless steel and defines a cylindrical support surface 26 which extends axially along the ring from a first end, up to a step 28. The internal support ring 22 has an externally threaded collar 30 at its second end, beyond the step 28.

The outer ring 24 is formed from a nickel titanium based shape memory alloy which is treated so that it can be heated to a temperature which is above the characteristic $A_f$ temperature of the alloy to cause the ring to contract radially.

Figure 9:
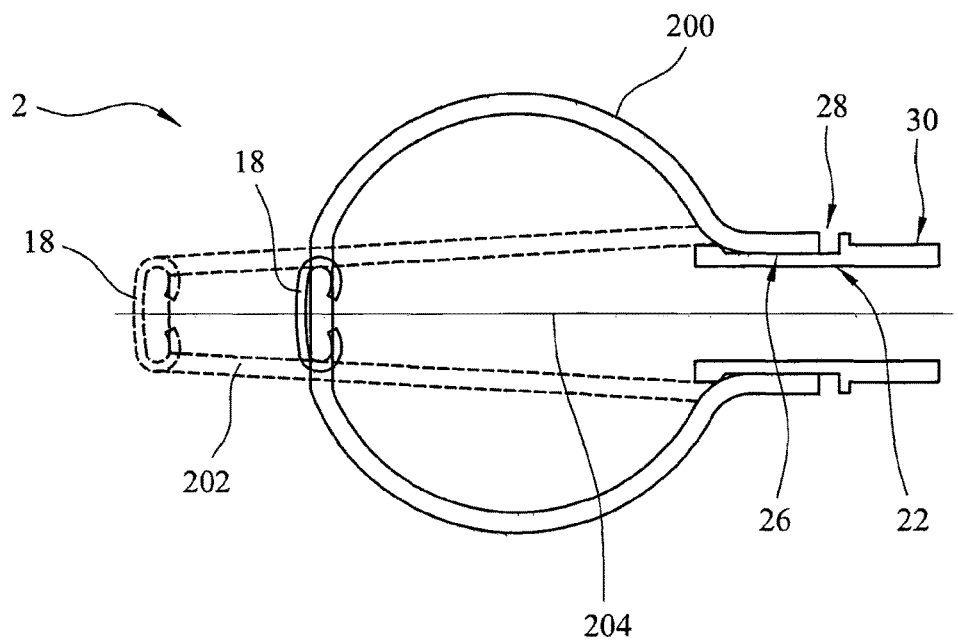
FIG. 9 shows a schematic side view illustrating the general shape of the deformable implant in its deployed and collapsed states.
Figure 10:
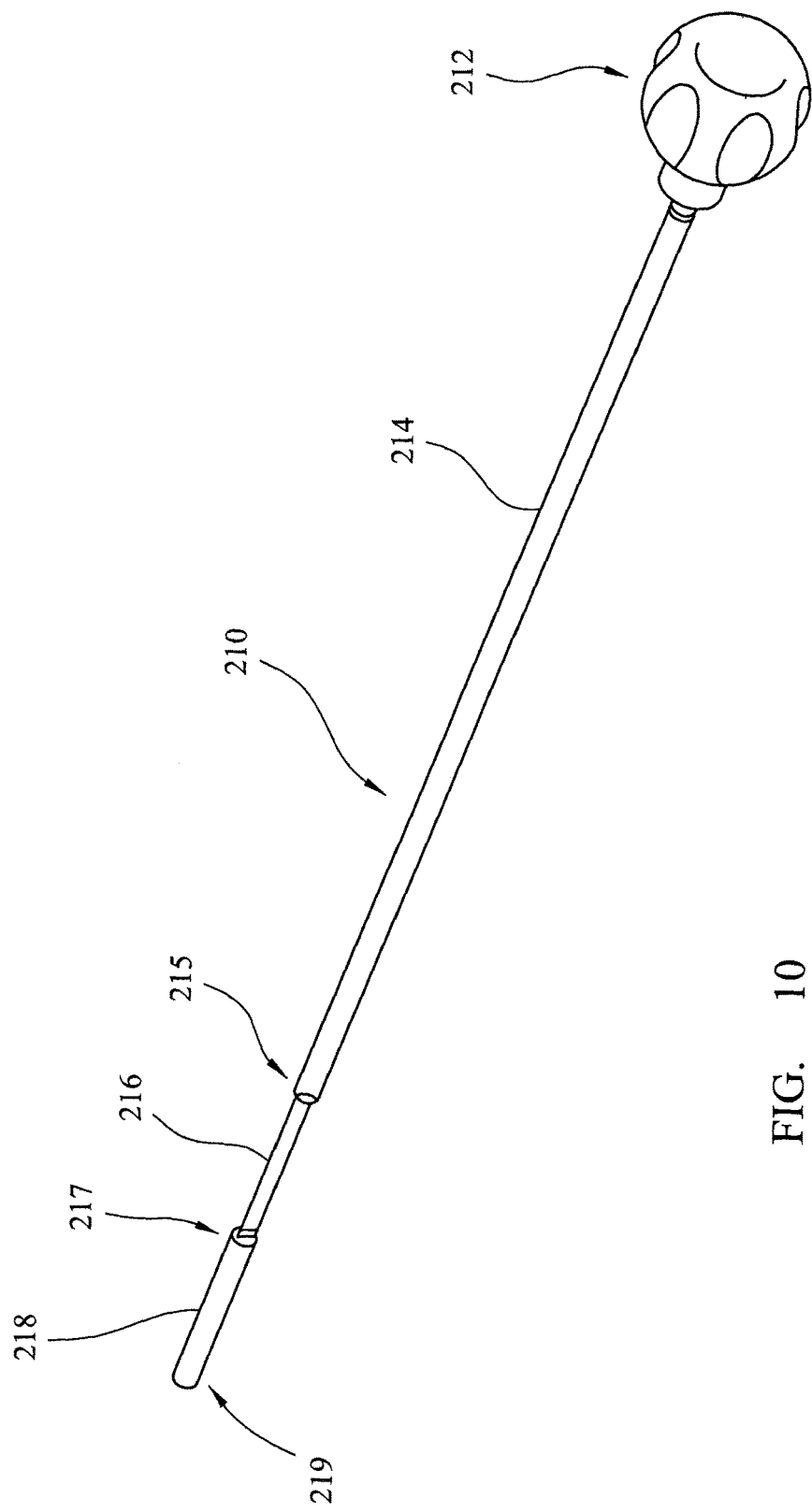
FIG. 10 shows a perspective view of an impactor instrument part of the kit of parts.

The implant 2 is generally similar to that described in WO 2010/097636, but the clip 18 differs in that it does not include a spigot or socket feature but rather presents any plain surface with which the distal end of the push rod can engage in order to deform the implant as described in greater detail below with reference to FIG. 9 in particular.

Operation of the inserter instrument will now be described with particular reference to FIG. 9. FIG. 9 shows a schematic cross sectional diagram of the deformable implant 2 in its generally circular deployed state 200 and also in its collapsed, insertion state 202. It will be appreciated that insertion state 202 is an approximation of the exact form adopted by the deformable implant for insertion. The exact form will depend, on a variety of factors, including the stiffness of the wires of the cage, the deformation force applied and the action of the clip 18 on the wires defining the cage. However, as illustrated in FIG. 9, in its deployed state 200, the implant has a generally wider and shorter form, than in its deformed, insertion state in which it is generally narrower and longer with respect to the longitudinal axis 204.

Prior to insertion of the deformable implant 2, a cavity is formed in the patient's bone having a generally spherical form and being approximately 1 mm smaller in the diameter than the diameter of the implant in its deployed state 200. This is to enhance the support provided by the implant and also the grip between the implant, when deployed, and inner surface of the bone cavity. In order to preserve bone stock, the cavity is created via a narrower channel through which the implant is inserted.

Initially, the implant 2 in its deployed state is attached to the distal end 102 of the insertion instrument 1 by engaging thread 30 into thread 108 and screwing them together until resistance is felt. The implant 2 is then slackened off by a quarter turn in order to facilitate eventual release of the implant 2 from the insertion instrument 1. The push rod 150 is then introduced into the instrument 100 via the proximal end 104 until the distal end 152 of the push rod engages the inner side of clip 18, as best illustrated in FIG. 3. The cap 132 of the drive mechanism is then threadingly engaged with thread 110 at the proximal end of the instrument and rotated. Eventually, the inner wall 140 of cap 132 will abut the proximal end 154 of the push rod. Further rotation of cap 132 will cause a driving force to be exerted on the push rod in the distal direction causing deformation of the implant 2 by the action of distal end 152 of the push rod on the inner surface of clip 18. Hence, the implant 2 will start to deform as illustrated in FIG. 9 by increasing its length and decreasing its transverse width. The cap 132 is rotated by the user until the implant has deformed sufficiently to snugly fit within the access tunnel to the spherical bone cavity. Pin 156 and channel 158 provide a push rod stop to prevent over extension of the push rod. Pin 156 prevents the push rod 150 from extending too far in the distal direction by engaging with the end face of channel 158 thereby preventing further extension of the push rod in the distal direction. Further, pin 156 in channel 158 prevents rotation of the push rod about the longitudinal axis of the cavity and relative to the body 100.

At some stage in the procedure, once the size of the deformable implant 2 has been selected, the insertion stop 122 is clamped about the body 100 at a scale position corresponding to the size of the attached implant. For example, different diameter implants can be provided. The greater the size of implant, the less the depth of insertion required by the instrument. Therefore, by adjusting the position of the inserter stop clamp 126, the depth of insertion of the instrument can be controlled. A guide tube (not shown) is provided into which the inserter instrument 1 and implant 2 are inserted. A proximal part of the guide tube provides an abutting surface against which stop 122 can abut to prevent further insertion of the inserter instrument into the patient's bone. Hence, inserter stop 126 helps to control the correct depth of insertion of the instrument to ensure that the implant is located at the correct depth in the cavity for deployment. The longitudinal position of the stop 122 along the longitudinal axis of the instrument 100 can be adjusted and the scale markings provide a visual guide to the user as to the correct position to place the stop corresponding to the size of implant 2 being used.

Once the implant has been inserted to the correct depth, the cap 132 can be rotated in the opposite direction through its drive rotation direction and the spring force of the implant 2 pushes against the distal end 152 of the push rod so as to urge the push rod 152 in the proximal direction. By continuing to unscrew cap 132, the cap 132 can eventually be removed from the instrument body 100 thereby exposing the proximal end 154 of the push rod. The push rod 150 can then be removed from the cavity of the body 100 while keeping the implant in position in the bone cavity.

A mixture of graft material can then be introduced into hopper 112. An impaction instrument 210 can then be used to drive bone graft material into the interior of the implant 2 within the bone cavity. Impaction instrument 210 includes a handle 212 at a proximal end. A proximal portion 214 extends from handle 212 in the form of a rod. Intermediate portion 216, in the form of a generally planar thin beam extends from proximal portion 214 to a distal portion 218 similarly in the form of a circular rod. The intermediate portion provides a visual indicator to a user to help prevent accidental removal of the impaction rod 210 during bone graft impaction. When a user sees the change in diameter between proximal portion 214 and intermediate portion 216, then they should stop withdrawal of the impaction rod 210 to ensure that it does not escape from the proximal end 104 of the instrument 100. The intermediate portion is positioned along the longitudinal axis of the impaction instrument 210, such that it will be visible out of the proximal end of the instrument 100, when the distal end of the impaction instrument 210 is adjacent the location of the hopper opening 116 so that bone graft material can pass into the instrument for impaction by pushing the impaction rod in the distal direction.

More specifically the length of distal portion 218 (between free end 219 and junction 217) is substantially the same as the distance between the proximal end 104 end surface and a rear end of opening 116. Hence, when junction 217 is just visible to a user out of the end 104 of the instrument, the distal end 219 will be just adjacent the rear end of hopper opening 116 which will not be clear and no longer occluded by the impaction instrument 210 at all. Hence, the user knows that the impaction instrument does not need to be further withdrawn in order to add bone graft. The distance between the distal end 219 and junction 215 is substantially the same as the distance between the proximal end 104 end surface and the forward end of opening 116. Hence, when junction 215 is just visible to a user out of the end 104 of the instrument, the distal end 219 will be adjacent the forward end of hopper opening 116 which is just starting to be cleared with the impaction instrument 210 in that position. Hence, the user knows that the impaction instrument only needs to be withdrawn a short further distance in order to fully clear opening 116. Hence, the junctions 215, 217 provide visual feedback to the user as to the position of the distal end 219 of the impaction instrument relative to the hopper opening and the extent to which the hopper opening is clear to add more bone graft to the instrument.

As explained above, a proximal part of the guide tube provides an abutting surface against which stop 122 can abut to control the depth of insertion of the inserter instrument into the patient's bone. During impaction of bone graft, the abutment of stop 122 against the guide tube also helps to reduce the transfer of impaction forces to the implant 2 thereby helping to avoid the position or shape of the implant form being affected. Hence, impaction forces created by the impaction instrument 210 being used to drive bone graft material into the bone cavity are largely transferred to the surface of the patient's bone by the action of impactor handle 212 being transferred via stop 122 to the guide tube which itself engages the patient's bone rather than the implant 2.

Impaction instrument 210 is used to impact sufficient bone graft material into the implant cavity as desired by the surgeon. In order to remove the insertion instrument 100, the insertion instrument is rotated about its longitudinal axis so as to unscrew implant 2 from the distal end 108 thread of the instrument 100. The frictional force between the implant 2 and the bone cavity helps to retain the implant 2 within the bone cavity thereby allowing removal of the instrument while retaining the implant in the bone cavity.

The instrument and parts thereof can be made from any suitable material, such as surgical grade stainless steel. Plastic materials can be used for the end cap 132, handle 212 and handle 130. Alternatively, metal components throughout can be provided.

The push rod 150 can have a length of approximately 450 mm and a diameter of approximately 5 mm. The insertion instrument 100 can have a length of approximately 400 mm. The diameter of the implant can range from approximately 18 mm to 26 mm in 2 mm increments.

As will be appreciated, the drive rod 150 is longer than the instrument body 100. As illustrated, the length of the drive rod 150 is approximately the length of the guide body plus the length of the implant 2 in its deformed state. The guide rod may be sufficiently long to encompass the full range of sizes of implant. Also, the guide rod is preferably sufficiently long to include the size of the largest implant 2 in its deformed state, the length of the instrument body and a slight excess of length to abut the inner surface 140 of the cap 132 so as to prevent the cap binding against the threaded proximal end 104 of instrument 100. The use of a cap in the form of a rotatable knob and using a threaded drive mechanism provides a particularly simple yet effective drive mechanism. Further, the cap 132 can be removed from the instrument to allow removal of the push rod 150 from the cavity thereby allowing the cavity also to be used to deliver bone graft material to the implant. Hence, there is no need to introduce or attach a secondary instrument in order to deliver bone graft into the implant.

Various modifications and variations will be apparent to a person of ordinary skill in the art from the above teaching. For example, other types of drive mechanism which can abut the proximal free end of the push rod to drive it distally may be provided.

The invention claimed is:

1. A kit of parts for inserting a deformable implant into a cavity in a bone of a patient, the kit of parts comprising:
   an inserter instrument comprising a body having a cavity extending along a longitudinal axis of the body from a distal end to a proximal end and including an attachment mechanism at the distal end to which a deformable implant can be releasably attached,
   a drive mechanism at the proximal end of the body, and an insertion stop mounted on the body and arranged to control the depth of insertion of the inserter instrument into a guide tube;
   a push rod slidably arranged within the cavity and having a distal end engageable with a part of the deformable implant and a proximal end abutable by the drive mechanism, wherein the drive mechanism is operable to drive the push rod toward the distal end of the body; and
   an impactor dimensioned for slidable engagement within the cavity;
   wherein the stop comprises:

a member extending from the push rod; and a channel in an inner wall of the body having an end wall, and wherein the member is arranged to slide within the channel and to abut against the end wall.

2. The kit of parts as claimed in claim 1, wherein a part of the drive mechanism is removable from the instrument and wherein the push rod is slidably removable from the instrument via the proximal end of the body.

3. The kit of parts as claimed in claim 1, wherein the push rod has longitudinal length greater than a longitudinal length of the cavity of the body.

4. The kit of parts as claimed in claim 1, wherein the drive mechanism includes an internal thread, an external thread co-operating with the internal thread and a cap, wherein the cap is arranged to abut the proximal end of the push rod and the cap includes a one of the internal thread and the external thread and the proximal end of the body includes the other of the internal thread and the external thread.

5. The kit of parts as claimed in claim 4, wherein the external thread is provided on an outer surface of the body at the proximal end of the body and the internal thread is provided on an inner surface of the cap.

6. The kit of parts as claimed in claim 4, wherein the cap includes a grip formation disposed around on an outer surface around its periphery providing a grip for rotation of the cap about the longitudinal axis by a user.

7. The kit of parts as claimed in claim 1, wherein the inserter instrument further comprises a hopper attached to an upper surface of the body and including a lower opening in communication with the cavity.

8. The kit of parts as claimed in claim 1, wherein the inserter instrument further comprises a flat upper surface extending along the body.

9. The kit of parts as claimed in claim 1 wherein the inserter instrument further comprises a scale including plurality of indicia on an outer surface of the body and indicating different depths of insertion of the instrument.

10. The kit of parts as claimed in claim 9, wherein the insertion stop is an adjustable insertion stop attachable to the scale at different longitudinal positions to control the depth of insertion of the inserter instrument.

11. A kit of parts as claimed in claim 1 wherein the impactor has an impactor longitudinal length greater than the length of the cavity.

12. The kit of parts as claimed in claim 11, wherein the impactor includes a distal part in the form of a rod and having a free end, an intermediate part in the form of a flat beam, a proximal part in the form of a rod, a handle attached to a proximal end of the proximal part and wherein the intermediate part is arranged between the distal part and the proximal part.

13. The kit of parts as claimed in claim 11 or H, and further comprising:

a deformable implant including a releasable attachment mechanism arranged to co-operate with the attachment mechanism of the distal end of the inserter instrument.

* * * * *